United States Patent
Diener et al.

(10) Patent No.: US 7,978,461 B2
(45) Date of Patent: Jul. 12, 2011

(54) ENHANCED ULTRASOUND SYSTEM

(75) Inventors: Alexander M. Diener, San Diego, CA (US); Bradley J. Sliger, Seattle, WA (US); Tom Lorusso, Seattle, WA (US); Jerry J. Van Eyck, Mill Creek, WA (US)

(73) Assignee: SonoSite, Inc., Bothell, WA (US)

( * ) Notice: Subject to any disclaimer, the term of this patent is extended or adjusted under 35 U.S.C. 154(b) by 582 days.

(21) Appl. No.: 11/852,196

(22) Filed: Sep. 7, 2007

(65) Prior Publication Data
US 2009/0069725 A1    Mar. 12, 2009

(51) Int. Cl.
*H05K 5/00* (2006.01)
*A61B 8/14* (2006.01)
*A61B 8/00* (2006.01)
*A61B 18/04* (2006.01)
*A61H 1/00* (2006.01)

(52) U.S. Cl. .................. 361/679.01; 600/459; 600/446; 601/2; 606/27

(58) Field of Classification Search .................. 600/459, 600/446; 361/679.01–679.45, 679.55–679.59; 601/2; 606/27; 312/223.1, 223.2; 29/592.1; D24/158
See application file for complete search history.

(56) References Cited

U.S. PATENT DOCUMENTS

| | | | |
|---|---|---|---|
| 5,404,267 A * | 4/1995 | Silva et al. ............... 361/679.03 |
| 5,640,960 A * | 6/1997 | Jones et al. .................. 600/453 |
| 5,738,099 A * | 4/1998 | Chang ........................ 600/437 |
| 5,840,012 A * | 11/1998 | Krauter et al. ............... 600/102 |
| 6,028,765 A * | 2/2000 | Swindler et al. .......... 361/679.55 |
| 6,139,496 A * | 10/2000 | Chen et al. ................... 600/437 |
| 6,139,502 A | 10/2000 | Fredriksen et al. |
| 6,151,207 A | 11/2000 | Kim et al. |
| D461,895 S * | 8/2002 | Barnes et al. ................ D24/158 |
| 6,532,152 B1 * | 3/2003 | White et al. .................. 361/692 |
| 6,540,685 B1 * | 4/2003 | Rhoads et al. ................ 600/459 |
| 2002/0143256 A1 * | 10/2002 | Wing et al. .................... 600/459 |
| 2003/0195418 A1 * | 10/2003 | Barnes et al. ................. 600/437 |
| 2005/0240102 A1 | 10/2005 | Rachlin et al. |
| 2006/0025684 A1 * | 2/2006 | Quistgaard et al. ........... 600/441 |
| 2006/0054335 A1 * | 3/2006 | Rapp et al. ...................... 174/48 |
| 2006/0079792 A1 * | 4/2006 | Finburgh et al. .............. 600/485 |
| 2006/0174065 A1 | 8/2006 | Kuzara et al. |
| 2006/0245152 A1 * | 11/2006 | Chauhan ....................... 361/681 |
| 2006/0274493 A1 * | 12/2006 | Richardson et al. .......... 361/683 |
| 2008/0250278 A1 * | 10/2008 | Zellner et al. ................. 714/712 |
| 2010/0016726 A1 * | 1/2010 | Meier ........................... 600/459 |

OTHER PUBLICATIONS

International Search Report and Written Opinion issued for PCT/US08/075012, dated Nov. 13, 2008, 9 pgs.

* cited by examiner

*Primary Examiner* — Jayprakash N Gandhi
*Assistant Examiner* — Nidhi Desai
(74) *Attorney, Agent, or Firm* — Perkins Coie LLP

(57) ABSTRACT

An enhanced ultrasound housing and enhanced ultrasound platform facilitates a technician-friendly layout by providing a beneficial ergonomic layout. Control switches may also be configured to provide convenient implementation of ultrasound techniques. Further, an enhanced ultrasound housing and enhanced ultrasound platform provides physical protection to the device. Physical protection may come in the form of an exoskeletal member, or from a covering which inhibits liquid penetration.

40 Claims, 4 Drawing Sheets

ENHANCED ULTRASOUND SYSTEM

TECHNICAL FIELD

The present application is directed towards ultrasound platforms, and more specifically to providing an ultrasound platform with improved physical protection.

BACKGROUND

Many current diagnostic and therapeutic ultrasound systems provide cart-based platforms where the display screen, user interface, and control switches are confined to a cart, often in an inconvenient location for a technician. This configuration forces the technician to twist, turn or reach between the platform and a patient being examined, resulting in a poor ergonomic setup for the technician.

These and other issues have led many ultrasound platform developers to create different platform configurations in an attempt to dispose one or more components of an ultrasound system for more convenient access by the technician. For example, portable platforms or platforms that are attached to an arm which can extend from the system closer to the patient have been developed. These solutions give the technician access to closer display screens and user interfaces. Unfortunately, many times even with these platforms that can be conveniently disposed with respect to the patient, the devices are still not laid out in an ideal ergonomic manner for the technician. Further, a technician may still need access to various tools and accessories such as a gel bottle, different probe, etc., thereby propagating the poor ergonomic situation.

Another issue occurs when providing an ultrasound platform for use off of a cart or table and closer to the patient, in that it is more exposed to possible hazards such as bumping or dropping the platform. Currently, relatively little has been done to meaningfully enhance a platform's ability to withstand mechanical impacts.

Additionally, dependent on the setting where the system is being used, there may be many different fluids proximate to the patient that could damage the platform if they came in contact with the platform (e.g. blood, ultrasound gel, etc.). Unwanted fluids may also create adverse health risks because bacteria and viruses may be present. While efforts have been made to address this issue, solutions have been limited when dealing with a platform that is disposed near the patient.

BRIEF SUMMARY

The present application is directed to systems, devices, and methods which utilize an exoskeletal member circumferentially disposed about ultrasound platform embodiments to provide mechanical support, protection from physical damage, and/or an ergonomic form factor. Embodiments of the present invention provide for mechanical support and physical protection of an ultrasound platform by either forming a housing of the platform within an exoskeletal member, or by at least partially framing the platform by an exoskeletal member. The exoskeletal member is preferably shaped and disposed to cover areas of the platform at the highest risk of sustaining damage from such an impact.

Depending on various needs of embodiments, the exoskeletal member may be made from a rigid material such as a metal or a hard plastic, or from a shock-absorbent material such as a soft plastic or rubber. Differing materials may be chosen based on factors that effect the exoskeletal member's functionality. For example, rigid materials may provide better mechanical support, while shock absorbent materials may provide better impact protection.

Further, in some embodiments, the exoskeletal member can frame the platform to define angled top and bottom portions. A platform including angled top and/or bottom portions provides a technician-friendly layout and improved ergonomics. For example, an ultrasound platform with an angled bottom portion may be configured to have the bottom portion extend toward the technician and house a user interface. This configuration functions to give a technician more convenient access to a user interface. Further, an ultrasound platform with an angled top portion may be formed such that the top portion extends away from the technician and comprise a handle which allows easy grip and/or movement of the platform. The top portion may additionally or alternatively be configured to hold tools or accessories that may be needed by the technician. In some embodiments the exoskeletal member may be the handle itself. The exoskeletal member may also be used to provide the means or cooperate with the ultrasound platform to hold said tools or accessories.

In some embodiments, the exoskeletal member provides the framework to attach a membranous cover. A membranous cover may serve to protect the platform from unwanted liquid penetration, facilitate easy cleaning of the platform, and/or serve to improve overall functionality of the platform. In some embodiments the membranous cover extends over some or all areas of the platform that have cracks, gaps, or seams which would allow fluids to enter into the housing, e.g. around control switches, user interfaces, displays, and the like.

Some embodiments of the present invention may serve to improve functionality of the platform by locating various control switches on the angled surfaces discussed above, or by the display screen. Placement of such control switches in various locations can facilitate convenient use of the platform for the technician. In some embodiments, control switches may be configurable by the end-user. While in other embodiments it may be advantageous to provide specialized control switches that are pre-configured to cause the switches to perform functions based on specific clinical applications to be implemented by the technician. For example, a technician may work in a office that uses the ultrasound system primarily for fetal monitoring. In this case, embodiments of the present invention may provide pre-configured control switches which correspond to frequently used functions for fetal monitoring, e.g., head measurements. Many specialties exist which may desire different functionality, other embodiments can include different configurations based on different these specialties.

In some embodiments, the switch configuration may be implemented by the placement of a cover on the platform. This cover may be the membranous cover discussed above. In these embodiments, the cover may be designed to interact with the platform when placed thereon, to indicate which switch configuration is to be implemented for the platform. Placement of the cover could be done during the manufacturing process, or the cover may be configured to be field changeable. Further, in some embodiments corresponding labels are placed proximate to the control switches. These labels are used to indicate the function of the control switches. The labels may be disposed next to the switches on the platform, or on an edge of a display screen on the platform. In some embodiments the labels may also be part a cover such as the membranous cover discussed above.

The embodiments discussed above provide advantages to the technician, as well as to the manufacturer of the platform. Each feature, either individually or combined may work to provide enhanced protection and stability to the platform.

Further, the features minimize the need for the technician to make awkward movements when performing an ultrasound, thereby providing an ergonomic environment and minimizing potential hazards to the platform and overall ultrasound system created during normal use. Embodiments also work to simplify the manufacturing process by allowing a single platform to be designed and built, which then can interact with a cover and be configured to work with various specialties accordingly.

The foregoing has outlined rather broadly the features and technical advantages of various embodiments of the present invention in order that the detailed description that follows may be better understood. Additional features and advantages of the will be described hereinafter which form the subject matter of the claims. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION

It should be noted that the figures that are discussed herein show many different features combined on a single ultrasound platform. This is shown for ease of explanation only, and should not be construed as limiting embodiments of the present invention to containing every feature as shown. One skilled in the art will recognize that different users will have different needs and a platform may be configured accordingly to utilize concepts of the present invention.

Figure 1:
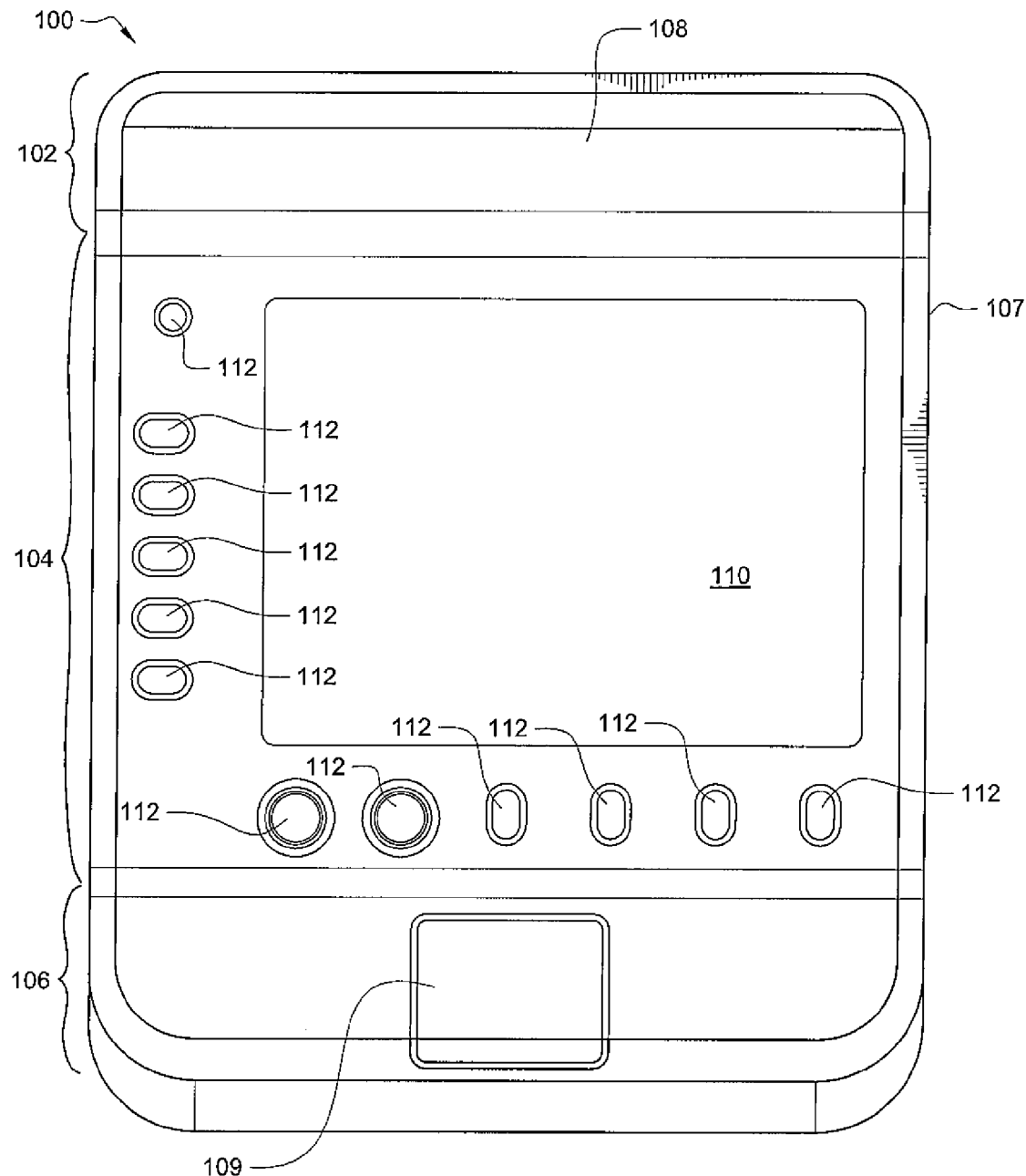
FIG. 1 is a front view of an ultrasound housing in accordance to an embodiment of the present invention.

FIG. 1 shows a front view of an ultrasound platform 100 according to a preferred embodiment of the present invention. Ultrasound platform 100 may be the type of platform used in systems such as ones used in diagnostic and/or therapeutic ultrasound.

Platform 100 of the illustrated embodiment has top portion 102, front portion 104, bottom portion 106, and exoskeletal member 107 circumferentially disposed thereon. Exoskeletal member 107 provides for enhanced protection of platform 100 and may also provide the framework for forming and/or supporting the other components in platform 100. For example, exoskeletal member 107 may be used to form and support portions of housing 100 and provide support for component parts of the ultrasound platform (i.e. display, user interface, underlying circuitry, etc.). In some embodiments, exoskeletal member 107 is a separate piece that connects to platform 100, which is configured to attach to platform 100 in order to provide enhanced protection and support for platform 100. In any case, exoskeletal member 107 at least partially frames the periphery of a housing of an ultrasound platform, such as platform 100, and provides enhanced protection to the platform from mechanical impacts.

Exoskeletal member 107 may be made of a shock absorbent material such as a soft plastic or rubber, or it may be made of a more rigid material such as a hard plastic or metal. The material used will depend on preferences of an end user and many factors can be considered. For example, a soft plastic or rubber material may provide better protection from minor bumps and other mechanical impacts of the ultrasound platform. Whereas a more rigid material may be better suited for providing a framework for components that exoskeletal member 107 may be supporting. Some materials will be heavier such as metal embodiments, while some are lighter such as plastic or rubber embodiments. In a portable platform situation, it is likely that a lightweight solution would be preferable as it gives the platform better mobility. The thickness of exoskeletal member 107 will also vary depending on the type of materials and considerations involved in the design and may range on the order of one or two millimeters up to three centimeters.

Figure 2A:
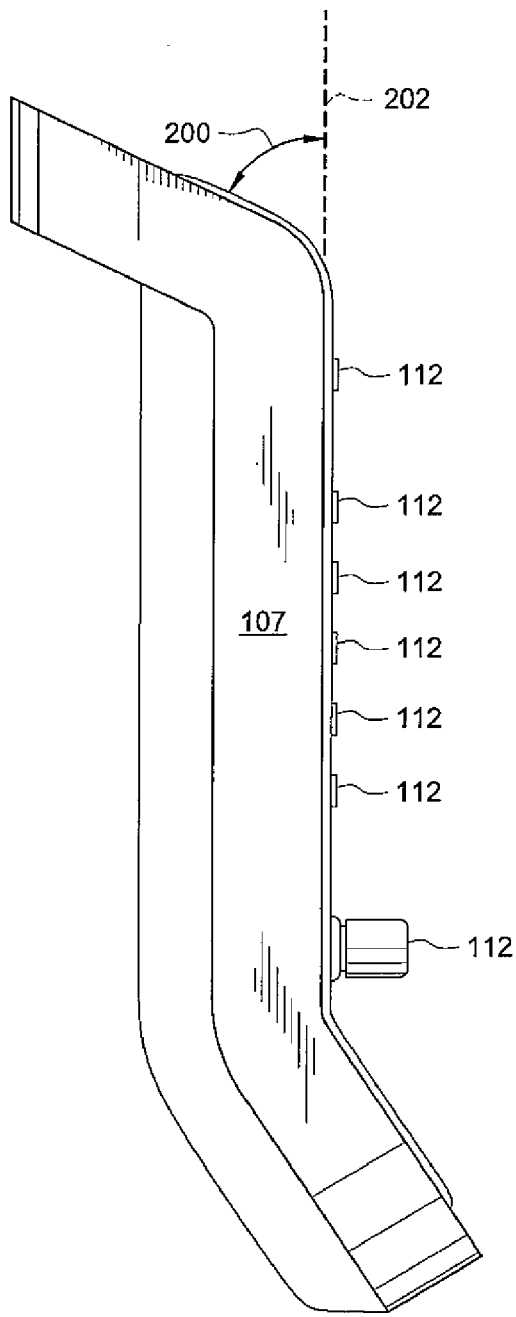
FIG. 2 illustrates side views of an ultrasound housing in accordance to an embodiment of the present invention.
Figure 2B:
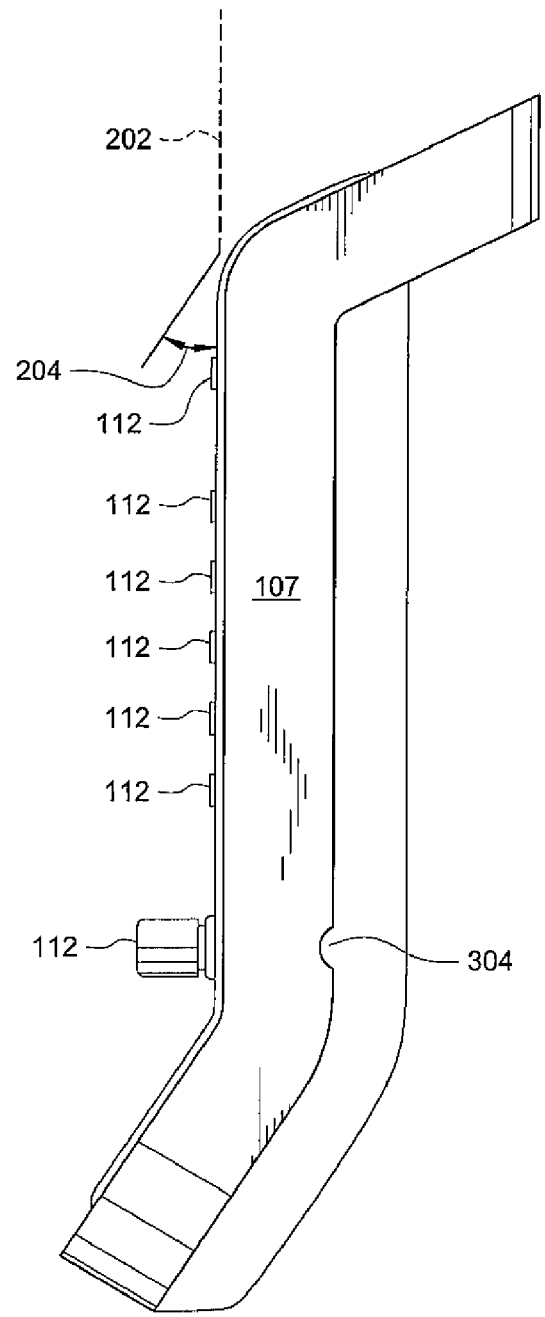

In some embodiments, exoskeletal member 107 frames platform 100 which includes angled top portion 102 and/or angled bottom portion 106 (see FIGS. 2A and 2B). Exoskeletal member 107 helps facilitate these angled portions by producing structural support at points that may be otherwise weak in these configurations. The angled portions may present several advantageous features.

Top portion 102 may extend at angle 200 behind the plane 202 created by front portion 104. Top portion 102 may be configured to be a handle for easy grip and movement of the platform 100. In some embodiments, such as illustrated in FIG. 1, exoskeletal member 107 may be configured to form the handle by creating a gap between upper surface 108 of top portion 102 and exoskeletal member 107.

In some embodiments, top portion 102 may be configured to hold various tools needed by an ultrasound technician such as a gel bottle or the ultrasound probe itself. Various clips or fasteners may be disposed on top portion 102 to facilitate holding of the tools. Top portion 102 may have one or more concave indents extending at least partially across the width of housing 100 at upper surface 110. The indents (not shown) may be configured to allow a tool, or any other accessory to rest thereon and give the technician easy access to the tool. For example, a gel bottle may be set on its side to rest on the concave indent. Exoskeletal member 107 may also be configured to cooperate with upper surface 108 to hold various tools and accessories used un the ultrasound process as discussed above. For example in the configuration of FIG. 1, the ultrasound gel bottle may rest on its side to be held between the edge of exoskeletal member 107 and upper surface 108.

Platform 100 of the illustrated embodiment further shows bottom portion 106. Bottom portion 106 of platform 100 may be configured to present a user interface, or portion thereof. For example, bottom portion 106 of the illustrated embodiment is configured to hold a user interface device 109. User interface device 109 shown is a touch-pad device, but it is contemplated that other forms of user interface are also suitable such as a keyboard, trackball, etc. Bottom portion 106 of the illustrated embodiment extends at a forward angle 204 with respect to the plane 202 of the front portion 104 (see FIGS. 2A and 2B). When bottom portion 106 is extended at forward angle 204 a technician using the ultrasound platform has an improved ergonomic situation because user interface device 109 is accessible without having to forcing the technician to bend his/her hand in an uncomfortable manner. Bottom portion 106 may also be pivotably connected to front portion 104. Many configurations may be implemented to create a pivotable connection. For example, a hinge may be disposed on bottom portion 106 and exoskeletal member 107 to facilitate movement. A pivotable connection will allow the angle of the bottom portion 106 to be adjustable for the convenience of the technician thereby further contributing to beneficial ergonomic form.

It is noted that the shape or dimensions of exoskeletal member 107 may vary depending on the type of platform with which exoskeletal member 107 is being implemented. For example, in some embodiments the housing 100 may not have any accompanying angular extensions on top portion 102 and/or bottom portion 106. In embodiments such as this, exoskeletal member 116 may be formed in a rectangular shape. On the other hand, as shown in the embodiments of FIGS. 2A and 2B, exoskeletal member 116 may be shaped to coincide with the angled extensions of the platform. Exoskeletal member 116 may be one single piece, or may comprise multiple portions. It may also be desirable to have the exoskeletal member 116 overhang one or more surfaces of the platform for enhanced edge protection.

Front portion 104 of platform 100 is configured to present a user interface, or portion thereof. For example, front portion 104 of the illustrated embodiment holds an ultrasound display 110. Display 110 can be any type of display which provides for functionality consistent with the concepts of the invention described herein. For example, display 110 may be an LCD, CRT, touch-screen, and the like. The front portion 104 may also be formed to house various control switches 112. Control switches 112 may be in the form of buttons, knobs, toggles, etc. Control switches 112 may have various functions depending on the type and use of the ultrasound system. For example, control switches 112 may be used to adjust aspects local to the ultrasound platform such as display contrast, brightness, and zooming. Further, control switches 112 may be used to aid a technician in measurement and imaging techniques. They may be programmable soft buttons which allow a user to change the function of a particular control switch 112, or they may be pre-configured to implement functions determined by the platform designer. For example, in a fetal monitoring setting a technician will often measure the head size of a fetus. A control switch may be configured to activate a measurement process such that when the technician indicates the reference points of the head, the system may output or display the measurement size. Numerous applications for which configurations exist that are specific to various medical specialties such as, measuring artery wall thickness, indicating the sex of a fetus, viewing and measuring Doppler flow, etc. In embodiments that use programmable soft button corresponding labels may be displayed on display 110.

Figure 3:
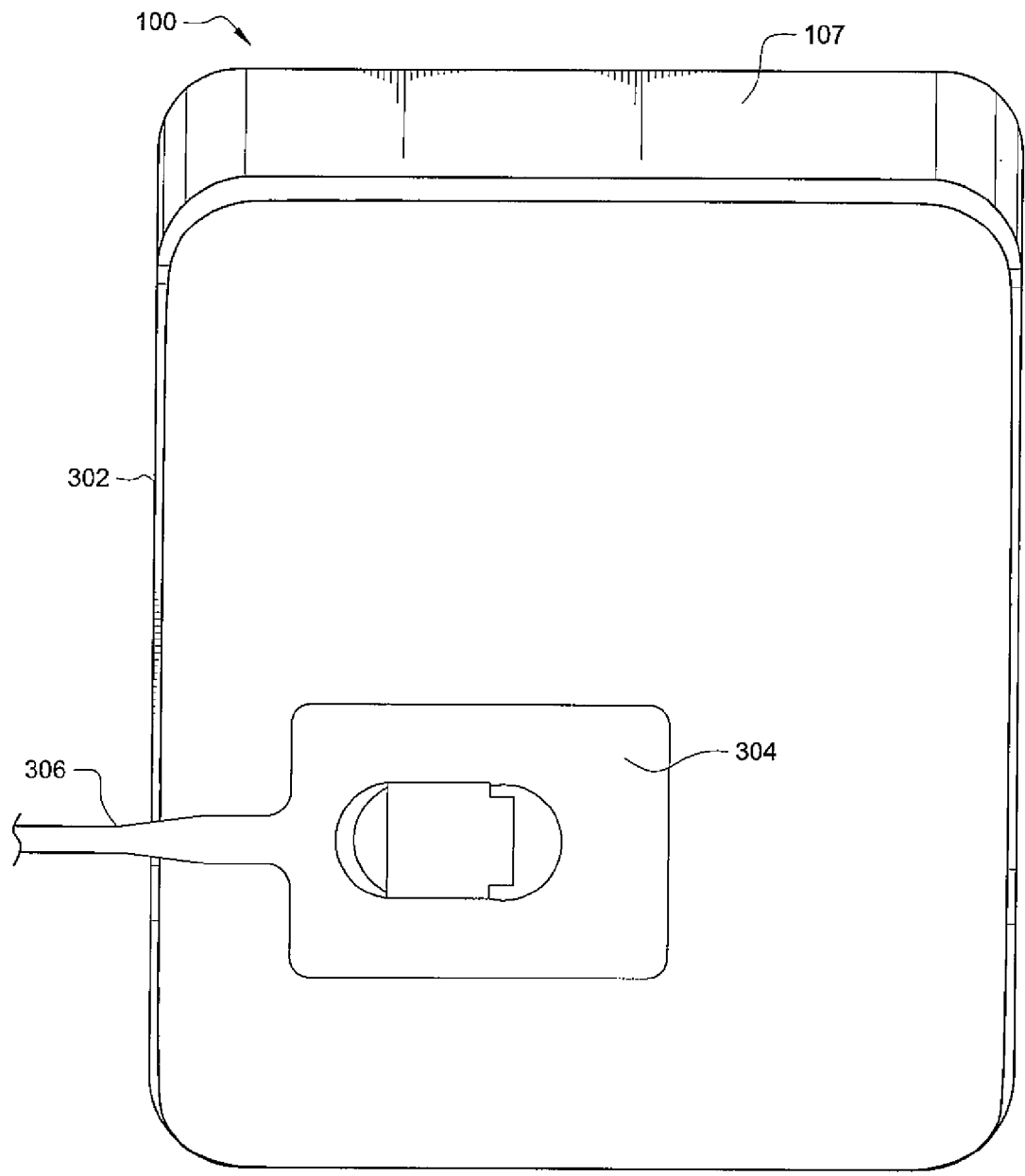
FIG. 3 is a rear view of an ultrasound housing in accordance to an embodiment of the present invention.

FIG. 3 shows rear surface 302 of ultrasound platform 100. Rear surface 302 of platform 100 shown in the illustrated embodiment includes an input interface 304 disposed thereon. Input interface 304 of a preferred embodiment provides a cable interface for an input cable 306, as may be used to couple the platform to additional components of the ultrasound system, such as one or more transducers. Interface 304 shown in FIG. 3 is described in U.S. Pat. No. 6,371,918 issued on Apr. 16, 2002, which is hereby incorporated by reference.

Such a interface allows embodiments of the present invention to share transducers with other ultrasound configurations as well as have various transducers connected through interface 304. One skilled in the art would recognize that input interface 304 may also be disposed on a side, bottom, or other location of housing 100. Locations that keep input cable 306 from interfering with the technician and overall ultrasound process are preferable.

Figure 4:
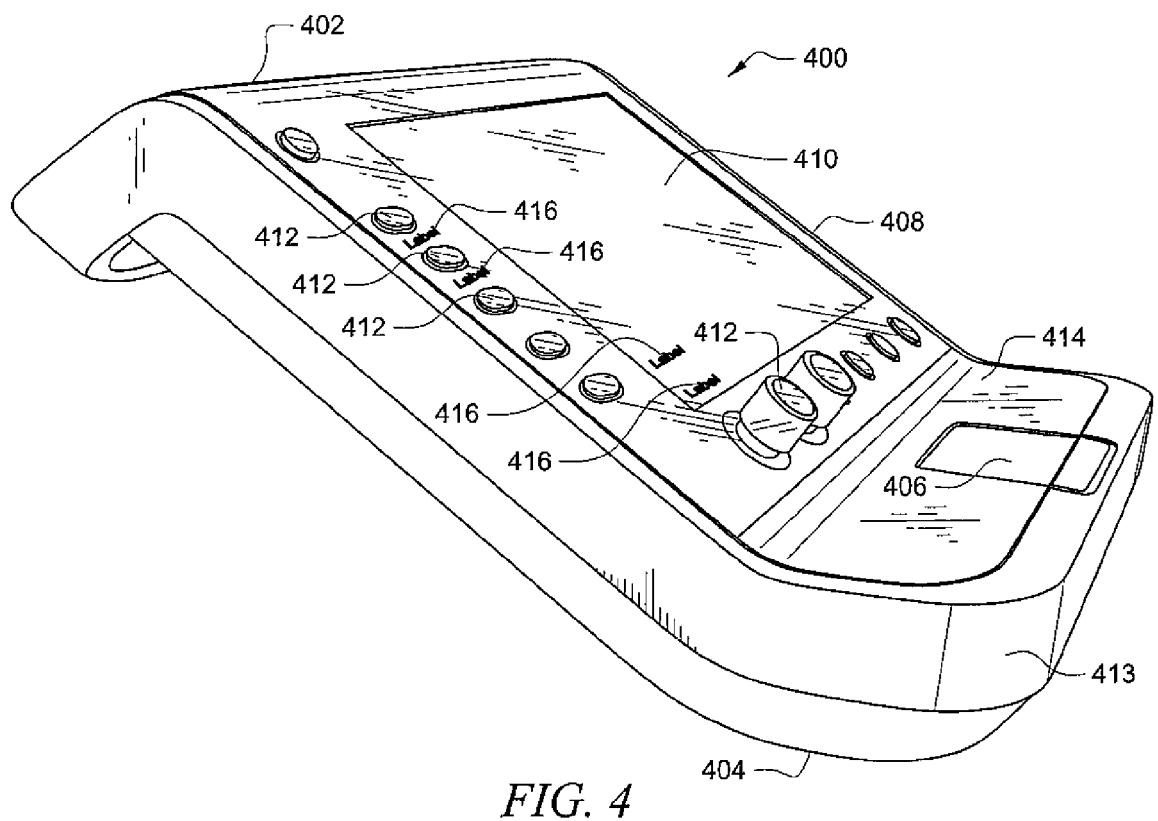
FIG. 4 is a perspective view of an ultrasound platform in accordance to an embodiment of the present invention.

FIG. 4 shows a perspective view of an ultrasound platform 400 in accordance with a preferred embodiment of the present invention. The illustrated embodiment shows an angled top portion 402 and an angled bottom portion 404 with a user interface 406. It further shows a front portion 408 with a display screen 410 and control switches 412. The illustrated embodiment also shows an exoskeletal member 413 circumferentially wrapping around the perimeter of the platform 400.

The front surface of the platform 400 is covered by membranous cover 414. In some embodiments, exoskeletal member 413 serves to hold the membranous cover 414 in place. As illustrated in the embodiment of FIG. 4, control switches 412 on the ultrasound platform 400 are also covered by membranous cover 414. This has the effect of eliminating any cracks or crevices that would lead down to the internal circuitry of platform 400. Embodiments including membranous cover 414 can partially cover the front surface of the ultrasound platform 400, or can fully cover the platform, including angled top 402, bottom 404 and front 408 portions, if such angled portions are applicable. The embodiment illustrated in FIG. 4 shows membranous cover 414 which covers the entire front surface of the ultrasound platform 400. Any area that is covered by membranous material 414 is provided better protection to outside hazards such as liquids spilled on the surface of the platform 400. It may also be preferable to provide a transparent cover over the display screen 410 and user interface 406. This transparent cover may be a continuous part of membranous cover 414, or could be a separate piece connected to the membranous cover 414 which is sealed together such that a liquid can not enter ultrasound platform 400 between the display 404 and/or user interface 406 and membranous cover 414.

The layout shown in FIG. 4 can also provide various functional advantages. It may be advantageous to equip platform 400 with pre-configured control switches that perform different functions based on various clinical applications that may be implemented by an ultrasound system. For example, when using an ultrasound system in a cardio/thoracic region of the body it may be helpful to the technician to have control switches directed toward the measurement of artery wall thickness, to the measurement of blood flow, etc. In contrast, in a fetal monitoring setting, it may be helpful to have functions to assist in measuring cranium size, indicating the sex of a child, etc. Some or all of these switches may be pre-configured during the assembly process as part of a specialized unit designed for specific clinical applications. Additionally, some or all of these switches may be programmable soft buttons that an end user may configure at a later time. In cases, implementing pre-configured switches or programmable soft buttons, labels 416 corresponding to the pre-configured control switches or programmable soft buttons may be placed proximate to control switches 412. Such labels 416 may be disposed on the elastomeric cover 414, or the display screen 410.

The configuration and/or labeling changes in some embodiments of the present invention may be done by the actual placing or changing the covering on the platform. For example, a membranous cover 414 may be provided which has labels corresponding to an ultrasound platform configured primarily for fetal monitoring applications. Membranous cover 414 may have an interface on its inner surface that interacts with the circuitry of the platform and informs the platform of the fetal monitor configuration thereby causing the control switches to be configured accordingly. Alternatively, a different membranous cover 414 may be provided which has labels corresponding to an ultrasound platform configured primarily for heart monitoring applications. This cover 414 may also have an interface on its inner surface that interacts with the circuitry of the platform and informs the platform of the heart monitor configuration thereby causing the control switches to be configured accordingly. Interfaces which interact with platform circuitry which inform the ultrasound system of the control switch configuration may be implemented by any means to accomplish this goal, many of such means are known in the art. For example, there may be a structure wherein the cover 414 plugs into the platform and the layout of the plug informs the platform which cover is present. Additionally or alternatively, cover 414 may have an RFID chip that is read by the system whereby the system is informed which cover is present based on the chip.

This cover may also simplify the manufacturing process, and improve potential marketability of the platform. For example, an ultrasound platform which is configurable by placing a cover on the top surface potentially allows a manufacturer to create a single ultrasound device which can be directed toward many different medical specialties based on pre-configurations that result by the placement of the cover. Further, this cover can improve marketing abilities as one would be able to sell the platform specifically to a target medical specialty group (e.g. fetal ultrasound device) based on the cover configurations which result in convenient functional advantages.

As can be seen, a cover such as the one shown in FIG. 4 may work to protect the ultrasound platform. The cover may also work to facilitate convenient use for the technician. As a result, this changeable cover can assist in providing an overall better ergonomic atmosphere, reduce the likelihood of technician endued accidents, and work to protect the ultrasound platform from external harm.

It is noted that various features described in the present application may stand alone, or be combined to create advantageous embodiments of the present invention. For example, an ultrasound platform having one or more angled extensions as discussed above may be implemented without the exoskeletal member. Further, while embodiments of the membranous cover is shown and described as being secured by the exoskeletal member, the cover may be implemented without such.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, means, methods and steps described in the specification. As one of ordinary skill in the art will readily appreciate from the disclosure of the present invention, processes, machines, manufacture, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, means, methods, or steps.

What is claimed is:

1. An ultrasound system, said ultrasound system comprising: a housing having a front portion configured to hold an ultrasound display; and an exoskeletal member attached to said housing, said exoskeletal member configured to at least partially frame said housing and provide external protection from mechanical impacts of said housing, wherein said housing is at least partially within said exoskeletal member and said exoskeletal member is adapted to provide structural support at weak points of said housing; wherein the ultrasound system comprising a bottom portion bounded on at least three sides by said exoskeletal member, said bottom portion extending at an angle in front of a plane defined by said front portion, said bottom portion configured to hold one or more user interface controls; wherein the ultrasound system comprising a top portion bounded on at least three sides by said exoskeletal member, said top portion forming a handle, extending at an angle behind a plane defined by said front portion; and wherein said exoskeletal member further comprises a hinge to facilitate movement of said exoskeletal member.

2. The ultrasound system of claim 1 wherein said front portion of said system is configured to hold at least one control switch.

3. The ultrasound system of claim 1 wherein said top portion is configured to receive at least one tool for a user of the ultrasound device.

4. The ultrasound system of claim 3 wherein said at least one tool may be one or more items selected from a list including: a gel bottle, and probe.

5. The ultrasound system of claim 1, wherein said handle is formed by said exoskeletal member.

6. The ultrasound system of claim 1 wherein said exoskeletal member comprises a shock-absorbent material.

7. The ultrasound system of claim 1 wherein said exoskeletal member is configured to hold a membranous cover.

8. The ultrasound system of claim 7 wherein said membranous cover interacts with said housing to configure one or more control switches to perform functions based on a specialized clinical application.

9. The ultrasound system of claim 8 wherein said membranous cover comprises a RFID chip to identify said membranous cover.

10. The ultrasound system of claim 1 wherein said exoskeletal member comprises metal.

11. The ultrasound system of claim 10 wherein said exoskeletal member comprises a metal band circumscribing said housing.

12. The ultrasound system of claim 1 wherein said exoskeletal member is adapted to provide an ergonomic form factor.

13. The ultrasound system of claim 1 wherein said exoskeletal member is adapted to cooperate with the ultrasound housing to hold any item from the group consisting of: a tool and an ultrasound system accessory.

14. An ultrasound system comprising:
a processing unit;
a housing;
a display;
at least one user interface, wherein said ultrasound housing comprises:
a front portion configured to secure the display;

a top portion configured for forming a handle, said top portion extending at an angle behind a plane defined by said front portion;

a bottom portion extending at an angle in front of the plane defined by said front portion, said bottom portion configured to secure said at least one user interface; and an exoskeletal member circumferentially around the housing and configured to cooperate with the top portion of the housing for forming said handle;

wherein said exoskeletal member further comprises a hinge to facilitate movement of said exoskeletal member.

15. The ultrasound system of claim 14 wherein said exoskeletal member comprises a shock-absorbent material.

16. The ultrasound system of claim 14 wherein said housing is at least partially covered by a membranous cover.

17. The ultrasound system of claim 16 wherein said membranous cover comprises a RFID chip to identify said membranous cover.

18. The ultrasound system of claim 14 wherein said front portion of said housing is configured to house at least one control switch.

19. The ultrasound system of claim 18 wherein said at least one control switch is pre-configured to perform different functions based on various clinical applications implemented by the ultrasound system.

20. The ultrasound system of claim 19 wherein said pre-configuration is implemented by placing a membranous cover on said housing.

21. The ultrasound system of claim 20 further comprising one or more labels proximate to said at least one control switch, said labels corresponding to said functions of said at least one control switch.

22. The ultrasound system of claim 20 wherein said front portion and control switches are at least partially covered by a membranous cover.

23. The ultrasound system of claim 14 wherein said top portion of said housing is configured to hold at least one tool for a user of the system.

24. The ultrasound system of claim 23 wherein said at least one tool may be one or more items selected from a list including: a gel bottle, and an ultrasound probe.

25. The ultrasound system of claim 14 wherein said bottom portion of said housing is pivotably disposed with said front surface thereby facilitating alteration of the inward angle of extension.

26. The ultrasound system of claim 14 wherein said exoskeletal member comprises metal.

27. The ultrasound system of claim 14 wherein said exoskeletal member is adapted to provide structural support to at least one weak point of said ultrasound housing.

28. The ultrasound system of claim 27 wherein said at least one weak point is caused by at least one of said angular extensions.

29. The ultrasound system of claim 14 wherein said exoskeletal member frames said housing to define said angled top and bottom portions.

30. The ultrasound system of claim 14 wherein said exoskeletal member comprises multiple portions.

31. The ultrasound system of claim 14 wherein said exoskeletal member is adapted to overhang one or more surfaces of said housing for enhanced edge protection.

32. The ultrasound system of claim 14 whereby a gap is provided between said exoskeletal member and said top portion.

33. A method for creating an ultrasound system, said method comprising the steps of: providing a housing having a front surface forming at least one aperture, a top portion and a bottom portion, said bottom portion angularly extending forward with respect a plane defined by said front surface, said top portion angularly extending backward with respect to the plane defined by said front surface; placing a display screen within said at least one aperture of said front surface of said housing, said display screen placed coplanar with said front surface of said housing; placing a user interface device within said bottom portion of said housing; and framing said housing within an exoskeletal member to structurally support said angular extensions; wherein said exoskeletal member comprises a hinge to facilitate movement of said exoskeletal member.

34. The method of claim 33 wherein said top portion is formed to serve as a handle for said system.

35. The method of claim 33 wherein said
exoskeletal member comprises a center section, an inwardly sloping section at one end of said center section and an outwardly sloping section at the other end of said center section; and wherein said front surface is supported by said center section, said bottom portion is supported by said inwardly sloping section, and said outwardly sloping section forms a handle for said system.

36. The method of claim 33 further comprising the step of placing at least one control switch within said at least one aperture of said front surface of said housing.

37. The method of claim 36 further comprising the step of covering said control switches and said front surface with a membranous cover.

38. The method of claim 36 further comprising the step of configuring said at least one control switch to perform a different function based on various clinical applications implemented by the ultrasound system.

39. The method of claim 38 further comprising the step of placing a label proximate to said at least one control switch, said labels corresponding to said functions of said at least one control switch.

40. The method of claim 33 wherein said exoskeletal member comprises metal.

* * * * *